United States Patent [19]

Mohamadi

[11] Patent Number: 5,248,691
[45] Date of Patent: Sep. 28, 1993

[54] FURANOINDOLINES

[75] Inventor: Fariborz Mohamadi, Indianapolis, Ind.

[73] Assignee: Eli Lilly and Company, Indianapolis, Ind.

[21] Appl. No.: 940,419

[22] Filed: Sep. 3, 1992

[51] Int. Cl.$^5$ .................. A61K 31/40; C07D 491/048; C07D 405/14; C07D 403/14
[52] U.S. Cl. ...................... 514/411; 548/430
[58] Field of Search ............ 548/430; 514/411

[56] References Cited

U.S. PATENT DOCUMENTS

| | | | |
|---|---|---|---|
| 4,169,888 | 10/1979 | Hanka et al. | 424/121 |
| 4,288,596 | 9/1981 | Kameyama | 548/430 |
| 4,912,227 | 3/1990 | Kelly et al. | 548/421 |

FOREIGN PATENT DOCUMENTS

| | | |
|---|---|---|
| 0154445 | 9/1985 | European Pat. Off. |
| 0359454 | 3/1990 | European Pat. Off. |
| WO88/04659 | 6/1988 | PCT Int'l Appl. |
| 91/11435 | 8/1991 | PCT Int'l Appl. |
| WO91/16324 | 10/1991 | PCT Int'l Appl. |

OTHER PUBLICATIONS

Martin et al., *J. Antibiot.*, 34, 1119 (1981).
Martin et al., *J. Antibiot.*, 33, 902 (1980).
Hanka, et al., *J. Antibiot.*, 31, 1211 (1978).
Reynolds, et al., *J. Antibiot.*, 39, 319 (1986).
Hurley, et al., *Acc. Chem. Res.*, 19, 230 (1986).
McGovren, et al., *J. Antibiot.*, 37, 63 (1984).
Wierenga, W., *Drugs of the Future*, 16, 741 (1991).
Li, et al., *Invest. New Drugs*, 9, 137 (1991).
Warpehoski, M. A., *Drugs of the Future*, 16, 131 (1991).
Li, et al., *Invest. New Drugs*, 5, 329 (1987).
Warpehoski, et al., *J. Med. Chem.*, 31, 590 (1988).
Wierenga, et al., *Adv. Enzyme Regul.*, 25, 141 (1986).
Warpehoski, M. A., *Tetrahedron Lett.* 27, 4103 (1986).
Ichimura, et al., *J. Antibiot.*, 43, 1037 (1990).
Ishii, et al, *J. Antibiot.*, 42, 1713 (1989).
Ogawa, et al., *J. Antibiot.*, 42, 1299 (1989).
Ohba, et al., *J. Antibiot.*, 41, 1515 (1988).
Martin, et al., *J. Antibiot.*, 38, 746 (1985).
Remers, W. A., *The Chemistry of Antitumor Antibiotics* John Wiley and Sons; New York, 1988; vol. 2; pp. 146-185.
Coleman, et al., *Studies in Natural Products Chemistry* 3, 301 (1989).
Scahill, et al., *Biochemistry*, 29, 2852 (1990).
Boger, et al., *J. Am. Chem. Sec.*, 112, 4623 (1990).
Kelly, et al., *J. Am. Chem. Sec.*, 109, 6837 (1987).
Boger, et al., *J. Am. Chem. Sec.*, 110, 4796 (1988).

*Primary Examiner*—Joseph Paul Brust
*Assistant Examiner*—MarySusan H. Gabilan
*Attorney, Agent, or Firm*—Robert A. Conrad; Leroy Whitaker

[57] ABSTRACT

This invention provides novel furanoindoline compounds effective in inhibiting the growth of solid tumors.

18 Claims, No Drawings

FURANOINDOLINES

BACKGROUND

Cancer is one of the leading causes of death in the United States. The American Cancer Society reports that about 494,000 people died from cancer in the United States in 1988. A common method of treatment for cancer is the use of chemotherapy. The use of chemotherapy has not been particularly successful in the treatment of solid tumors. Accordingly, there is a substantial need for new drugs which are effective in inhibiting the growth of such tumors.

It has now been found that a new group of furanoindolines have been effective in inhibiting the growth of solid tumors.

CC-1065 is an antitumor antibiotic that was isolated from the fermentation cultures of *Streptomyces zelensis* in 1978. See Martin, et al., *J. Antibiot.* 1981, 34, 1119; Martin, et al., *J. Antibiot.* 1980, 33, 902; Hanka, et al., *J. Antibiot.* 1978, 31, 1211. This molecule is an exceptionally potent cytotoxic agent that binds covalently to the minor groove of double stranded DNA and has good in vitro and in vivo pharmacology. For a review of the chemistry, biosynthesis, pharmacology and toxicology of CC-1065, see Reynolds, et al., *J. Antibiot.* 1986, 39, 319; Hurley, et al., *Acc. Chem. Res.* 1986, 19, 230.

Unfortunately administration of a single intravenous subtherapeutic dose of CC-1065 led to delayed deaths of healthy mice as a result of the hepatotoxicity of this molecule. McGovren, et al., *J. Antibiot.* 1984, 37, 63. This preempted the clinical development of CC-1065, but synthesis of fragments and analogs of CC-1065 elucidated the structural variables responsible for this undesirable hepatotoxicity and culminated in the clinical development of U-71184 and U-73975 at Upjohn. Wierenga, W. *Drugs of the Future* 1991, 16, 741; Li, et al., *Invest. New Drugs* 1991, 9, 137: Warpehoski, M. A. *Drugs of the Future,* 1991, 16, 131; Li, et al., *Invest. New Drugs* 1987, 5, 329; Warpehoski, et al., *J. Med. Chem.* 1988, 31, 590; Wierenga, et al., *Adv. Enzyme Regul.* 1986, 25, 141; Warpehoski, M. A. *Tetrahedron Lett.* 1986, 27, 4103. Kyowa Hakko Kogyo has since initiated an effort in the fermentation of molecules in this class and has isolated a number of natural products with very promising pharmacology. Ichimura, et al., *J. Antibiot.* 1990, 43, 1037; Ishii, et al., *J. Antibiot.,* 1989, 43, 1713; Ogawa, et al., *J. Antibiot.* 1989, 42, 1299; Ohba, et al., *J. Antibiot.* 1988, 41, 1515.

This invention provides novel furanoindoline compounds effective in inhibiting the growth of solid tumors.

SUMMARY OF THE INVENTION

This invention provides compounds of the Formula

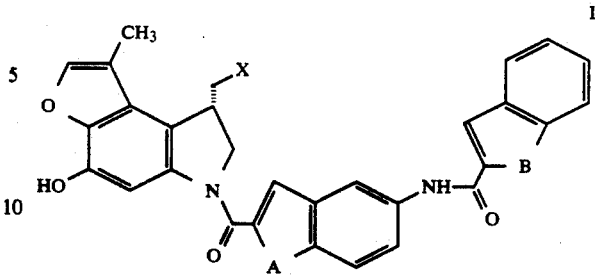

wherein
X is I, Br, Cl or OSO₂CH₃; and
A and B are independently NH, 0, or S.

This invention also provides a method for treating susceptible neoplasms in a mammal which comprises treating a mammal in need of such treatment with an effective amount of a compound of Formula I.

Also provided by this invention are pharmaceutical formulations useful for treating susceptible neoplasms comprising an effective amount of a compound of Formula I in combination with one or more pharmaceutically acceptable excipients, carriers, or diluents therefor.

DETAILED DESCRIPTION AND PREFERRED EMBODIMENT

Preferred compounds of the instant invention are those of Formula I in which X=Cl. Also preferred are those compounds wherein A=NH. Compounds which are most preferred are (+)-(1R)-1,2-dihydro-1-(chloromethyl)-3-(2 carbonyl-5-(amino-N-(2-carbonyl-1H-indole))-1H-indole)-5-hydroxy-8-methyl-3H-furano[3,2-e]indole, (+)-(1R)-1,2-dihydro-1-(chloromethyl)-3-(2-carbonyl-5-(amino-N-(2-carbonyl[B]benzofuran))-1H-indole)-5-hydroxy-8-methyl-3H-furano[3,2-e]indole, and (+)-(1R)-1,2-dihydro-1-(chloromethyl)-3-(2-carbonyl-5-(amino-N-(2-carbonyl[B]benzothiophene))-1H-indole)-5-hydroxy-8-methyl-3H-furano[3,2-e]indole.

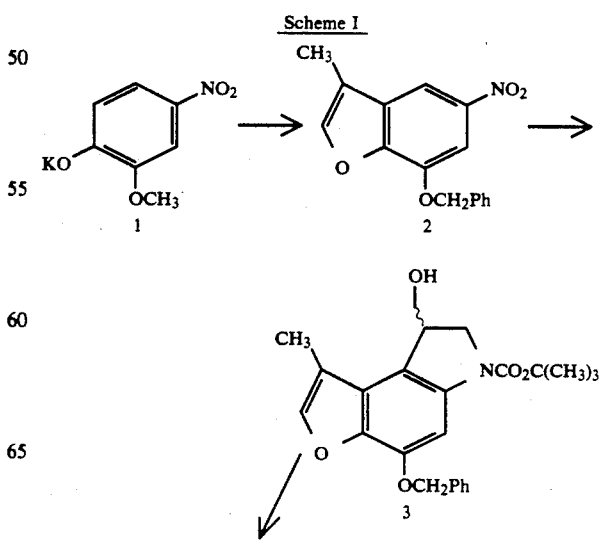

Scheme I

-continued
Scheme I

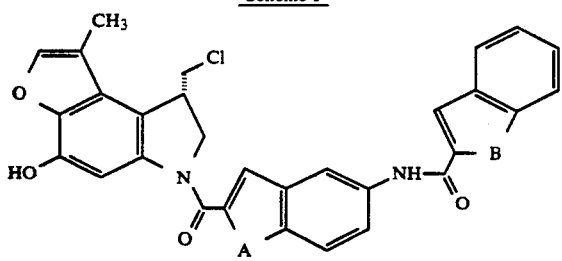

4 A = NH, B = NH
5 A = NH, B = O
6 A = NH, B = S
7 A = O,  B = NH
8 A = O,  B = O
9 A = O,  B = S
10 A = S, B = NH
11 A = S, B = O
12 A = S, B = S

The preparation of compounds of Formula I is accomplished by first alkylating the commercially available potassium salt of 4-nitroguaiacol (1) with crotyl bromide and subjecting the resulting crotyl ether to a thermolytic Claisen rearrangement to provide 6-(butenyl)-4-nitroguaiacol. Cleavage of the carbon carbon double bond with ozone followed by a reductive workup provides a benzylic aldehyde that undergoes dehydration to provide 3-methyl-5-nitro-7-methoxybenzofuran (2). Pyridine hydrochloride mediated demethylation followed by treatment of the hydroxybenzofuran with sodium hydride and benzyl bromide provides the desired 3-methyl-5-nitro-7-(benzyloxy)benzofuran. Catalytic hydrogenation with platinum oxide is used to reduce the nitro group and the crude product of this reaction is treated with di-t-butyl dicarbonate to provide 3-methyl- 5-N-(t-butyloxycarbonyl)amino-7-(benzyloxy)benzofuran. Electrophilic aromatic bromination of the molecule placed a bromine at the 4 position of this benzofuran as demonstrated by the collapse of the NMR doublet of the methyl group at the 3 position to a singlet. Treatment of the bromination product with propargyl bromide and sodium hydride provides 3-methyl-4-bromo-5-(N-(t-butyloxycarbonyl)-N-(2-propyn-1yl))amino-7-(benzyloxy)benzofuran. Treatment of this molecule with the Boger free radical cyclization/hydroboration (boger, et al., *J. Org. Chem.* 1990, 55, 5823) provides the desired racemic hydroxymethyl compound 3.

The racemic hydroxymethylfuranoindoline 3 can be resolved via its (R)-(−)-O-acetylmandelate by preparative high pressure liquid chromatography (HPLC). Treatment of the (+)-3 with carbon tetrachloride and triphenylphosphine followed by catalytic debenzylation provides (+)-(1R)-1,2-dihydro-1- (chloromethyl)-3-(t-butyloxycarbonyl)-5-hydroxy-8-methyl-3H-furano[3,2-e]indole. Deprotection of the nitrogen with hydrochloric acid followed by 1-(3-dimethylaminopropyl)-3-ethylcarbodiimide hydrochloride (EDCI) mediated coupling with the appropriate arylcarboxylic acid provides compounds of Formula I wherein X is chloro. Compounds wherein X is bromo are prepared in the same manner as above except that carbon tetrabromide is used in place of carbon tetrachloride. The mesyl compounds of Formula I (X=OSO$_2$CH$_3$) are prepared by reacting the hydroboration/oxidation product 3 with methanesulfonyl chloride, triethylamine, and methylene chloride at 0° C. The iodo compounds of this invention (X=I) can be prepared by heating the corresponding mesyl compound at reflux in the presence of sodium iodide and acetone.

The appropriate arylcarboxylic acid is synthesized by the coupling of indole-2-carboxylic acid, benzofuran-2-carboxylic acid or benzothiophene-2-carboxylic acid with ethyl 5-amino-aryl-2-carboxylate in DMF with EDCI, and saponification of the ester. Ethyl 5-aminoindole-2-carboxylate is formed by catalytic hydrogenation of ethyl 5-nitroindole-2-carboxylate (Parmerter, S. M.; Cook, A. G.; Dixon, W. B. *J. Am. Chem. Soc.* 1958, 80, 4621). Ethyl 5-aminobenzothiophene-2-carboxylate can be synthesized as described in: Zambias, R. A.; Hammond, M. L. *J. Syn. Commun.* 1991, 21, 959. Ethyl 5-aminobenzofuran-2-carboxylate is prepared from the commercially available 5-nitrobenzofuran-2-carboxylic acid.

The starting materials and intermediates for the preparation of the compounds of the present invention are commercially available or can be readily prepared by the above-described methods or other methods known in the literature. References to specific literature procedures are cited in the examples and listed following the example section hereinbelow.

The following examples further illustrate the preparation of the compounds of this invention. The examples are provided for purposes of illustration only and are not be construed as limiting the scope of the instant invention in any way.

The terms and abbreviations used in the instant examples have their normal meaning unless otherwise designed, for example, "THF" means tetrahydrofuran; "°C" refers to degrees Celsius; "N" refers to normal or normality; "mmol" refers to millimole; "g" refers to gram; "L" refers to liter; "mL" means milliliter; "M" refers to molar; "NMR" refers to nuclear magnetic resonance; "MS" refers to mass spectrometry.

Preparation of
1-(oxa-1-(2-butenyl))-2-methoxy-4-nitrobenzene.

A mixture of 4-nitroquaiacol, potassium salt hydrate (200 g, 0.97 mol) and crotyl bromide (175 g, 1.16 mol) was refluxed in 2 L of acetone overnight. The solvent was removed under vacuum and the residue filtered through silica gel (2 L) with 15% ethyl acetate in hexanes. The filtrate was collected in 4 L fractions and the appropriate fractions were concentrated under vacuum to provide 195 g of solid (91% yield). MS (FD) m/z 223 (M+).

Preparation of
2-(3-(1-butenyl))-4-nitro-6-methoxyphenol.

A solution of 1-(oxa-1-(2-butenyl))-2-methoxy-4-nitrobenzene (194 g, 0.87 mol) dissolved in 1.8 L of toluene was heated in a stainless steel bomb at 180° C. overnight. The reaction was cooled to room temperature and concentrated under vacuum. The residue was dissolved in 2 L of diethyl ether and extracted with 1.5 L of 1N sodium hydroxide. The aqueous layer was separated, acidified (pH 2) with 5N hydrochloric acid and extracted with methylene chloride. The organic layer was filtered through silica gel (2 L) with 15% ethyl acetate in hexanes and the appropriate fractions combined and concentrated under vacuum. The residue was triturated with hexanes to provide 108 g of solid (56% yield). Anal. Calcd for $C_{11}H_{13}NO_4$: C, 59.19; H, 5.87; N, 6.27. Found: C, 59.17; H, 5.86; N, 6.24.

Preparation of 3-methyl-5-nitro-7-methoxybenzofuran.

A stream of 3% ozone/oxygen was bubbled through a solution of 2-(3-(1-butenyl))-4-nitro-6-methoxyphenol (63.3 g, 0.284 mol) dissolved in 2 L of methylene chloride at −78° C. until the solution turned light blue (approximately 2 hours). The solution was purged with a stream of nitrogen at −78° C. and dimethylsulfide (62 mL) was added and the reaction stirred at ambient temperature for 30 minutes. The reaction was placed in a separatory funnel and the organic layer was washed with water (2×1 L). The methylene chloride layer was dried with anhydrous magnesium sulfate, filtered and concentrated under vacuum. The residue was added to a solution of polyphosphoric acid (60 g) dissolved in 1 L of benzene and stirred at reflux for 6 hours. The reaction was extracted with water (2×500 mL), the organic layer was dried with anhydrous magnesium sulfate, filtered and concentrated under vacuum. The residue was purified by a preparative high pressure liquid chromatogram (Waters Prep 500 A) with elution of 7.5% ethyl acetate in hexanes on two silica gel cartridges to provide 26.5 g of solid (45% yield). Anal. Calcd for $C_{10}H_9NO_4$: C, 57.97; H, 4.38; N, 6.76. Found: C, 58.81; H, 4.51; N, 6.84.

Preparation of 3-methyl-5-nitro-7-(benzyloxy)benzofuran (2).

A mixture of 3-methyl-5-nitro-7-methoxybenzofuran (39.1 g, 189 mmol) and pyridinium hydrochloride (130 g, 1.12 mol) were melted in a 170° C. oil bath under nitrogen for 2 hours. The reaction was cooled to room temperature, dissolved in 500 mL of methylene chloride, extracted with water (2×300 mL) and 1N sodium hydroxide (3×150 mL). The methylene chloride layer was dried with anhydrous sodium sulfate, filtered and concentrated under vacuum to provide 15.6 g of starting material (this material is recycled). The sodium hydroxide layer was acidified with 1N hydrochloric acid (585 mL) and extracted with methylene chloride (3×300 mL). The combined organic layer was dried with anhydrous sodium sulfate, filtered and concentrated under vacuum to provide 24.3 g of solid. To this precipitate and benzyl bromide (15.5 mL, 130 mmol) dissolved in 250 mL of anhydrous N,N-dimethylformamide (DMF) was added 55% sodium hydride/oil (5.7 g, 130 mmol). This mixture was stirred under a drying tube for 5 hours. The reaction was concentrated under vacuum, dissolved in 1 L of methylene chloride. The organic layer was washed with water (3×300 mL), dried with anhydrous sodium sulfate, filtered and concentrated under vacuum to provide 25.5 g of solid. Subjecting the 15.6 g of isolated starting material to the above procedure provided an additional 12 g of product (70% combined yield). This material was used crude in the next procedure.

Preparation of 3-methyl-5-N-(t-butyloxycarbonyl)amino-7-(benzyloxy)benzofuran.

A solution of 3-methyl-5-nitro-7-(benzyloxy)benzofuran (10 g, 35 mmol) and platinum oxide (3 g) in 200 mL of ethyl acetate was hydrogenated at 20 p.s.i. of hydrogen for 1.5 hours. The reaction was filtered through a plug of Celite ® and concentrated under vacuum. This residue and di-t-butyldicarbonate (15.4 g, 70.7 mmol) were dissolved in 130 mL of 1,4-dioxane and the mixture refluxed under nitrogen for 3 hours. The reaction was concentrated under vacuum and purified by flash chromatography with 15% ethyl acetate in hexanes to provide 8.0 g of solid (64% yield). Anal. Calcd for $C_{21}H_{23}NO_4$: C, 71.37; H, 6.56; N, 3.76. Found: C, 71.27; H, 6.48; N, 4.08.

Preparation of 3-methyl-4-bromo-5-N-(t-butyloxycarbonyl)amino-7-(benzyloxy)benzofuran.

To a solution of 3-methyl-5-N-(t-butyloxycarbonyl)amino-7-(benzyloxy)benzofuran (8.0 g, 22.0 mmol) dissolved in 120 mL of anhydrous tetrahydrofuran (THF) cooled to −61° C. (chloroform/dry ice) was added one drop of concentrated sulfuric acid and N-bromosuccinimide (4.0 g, 22.0 mmol). This mixture was stirred at −61° C. for 5 hours, then warmed to room temperature. The reaction was concentrated under vacuum and purified by flash chromatography with 10% ethyl acetate in hexanes to obtain 8.7 g of solid (92% yield). Anal. Calcd for $C_{21}H_{22}BrNO_4$: C, 58.34; H, 5.13; N, 3.24. Found: C, 58.54; H, 5.27; N, 3.18.

Preparation of 3-methyl-4-bromo 5-(N-(t-butyloxycarbonyl)-N-(2-propyn-1-yl))amino-7-(benzyloxy)benzofuran.

To a solution of 3-methyl-4-bromo-5-N-(t-butyloxycarbonyl)amino-7-(benzyloxy)benzofuran (8.7 g, 20 mmol) and an 80% toluene solution of propargyl bromide (8.9 g, 60 mmol) dissolved in 130 mL of anhydrous DMF was added 60% sodium hydride in oil (0.84 g, 21 mmol). This mixture was stirred at room temperature for 3 hours. The reaction was concentrated under vacuum, dissolved in 1 L of toluene and extracted with water (3×300 mL). The organic layer was dried with anhydrous sodium sulfate, filtered and concentrated under vacuum. The residue was purified by flash chromatography with 12.5% ethyl acetate in hexanes to obtain 9.0 g of oil (96% yield). MS(FD) m/z 469 (M+) and 471 (M+2).

Preparation of (+)-(1R)-1,2-dihydro-1-(hydroxymethyl)-3-(t-butyloxycarbonyl)-5-(benzyloxy)-8-methyl-8-methyl-3H-furano[3,2-e]-indole ((+)-3).

A solution of 3-methyl-4-bromo-5-(N-(t-butyloxycarbonyl)-N-(2-propyn-1-yl))amino-7-(benzyloxy)benzofuran (8.7 g, 18.5 mmol), tri-n-butyltin hydride (9.9 mL, 37 mmol) and 2,2'-azobis(2-methylpropionitrile) (0.62 g) in 320 mL of anhydrous benzene was refluxed for 35 minutes. The reaction was cooled to room temperature and concentrated under vacuum. To this residue was added a ~0.7 M THF solution of monoiso-pinocampheylborane (38.2 mmol, prepared from S-alpine boramine) and the reaction stirred at room temperature under nitrogen for 2 hours. The reaction was cooled to 0° C. and to it were added sequentially dropwise water (20 mL), 2N sodium hydroxide (20 mL) and 30% hydrogen peroxide (13 mL). This mixture was stirred at room temperature for 1 hour and 50° C. for 20 minutes. The reaction was extracted with diethyl ether (3×100 mL), the ether layer dried with anhydrous magnesium sulfate, filtered and concentrated under vacuum. The aliphatic tin byproducts were removed by dissolving this residue in acetonitrile and extracting with hexanes. The acetonitrile layer was concentrated under vacuum and the resulting foam purified by flash chromatography with 45% ethyl acetate in hexanes to provide 2.95 g of foam. This material had an enantiomeric excess of 50% of the (+)-(1R) isomer. Although further purification could be achieved by preparative high pressure liquid chromatography of the (R)-(−)-O-acetylmandelate derivative of this foam, recrystallization of the enhanced diastereomeric mixture from ether followed by lithium hydroxide mediated removal of the chiral auxiliary provided 1.32 g of solid (17.5% overall yield).

Anal. Calcd for $C_{24}H_{27}NO_5$: C, 70.40; H, 6.65; N, 3.42.

Found: C, 70.68; H, 6.83; N, 3.31. $[\alpha]_{589}$ +19.8° (c=0.35 mg/dL, $CH_2Cl_2$).

Preparation of (+)-(1R)-1,2-dihydro-1-(chloromethyl)-3-(t-butyloxycarbonyl)-5-(benzyloxy)-8-methyl-3H-furano[3,2-e]-indole.

To a solution of (+)-(1R)-1,2-dihydro-1-(hydroxymethyl)-3-(t-butyloxycarbonyl)-5-(benzyloxy)-8-methyl-3H-furano[3,2-e]indole (0.47 g, 1.15 mmol) dissolved in 5 mL of anhydrous methylene chloride were added triphenylphosphine (0.6 g, 2.3 mmol) and carbon tetrachloride (0.67 mL, 6.9 mmol). This mixture was stirred under nitrogen at room temperature overnight. The reaction was concentrated under vacuum and purified by flash chromatography with 7% ethyl acetate in hexanes to obtain 493 mg of solid (quantitative yield). Anal. Calcd for $C_{24}H_{26}ClNO_4$: C, 67.36; H, 6.12; N, 3.27. Found: C, 67.51; H, 6.36; N, 3.22. $[\alpha]_{589}$ −5.5° (c=0.36 mg/dL, $CH_2Cl_2$).

Preparation of (+)-(1R)-1,2-dihydro-1-(chloromethyl)-3-(t-butyloxycarbonyl)-5-hydroxy-8-methyl-3H-furano[3,2-e]indole.

To a solution of (+)-(1R)-1,2-dihydro-1-(chloromethyl)-3-(t-butyloxycarbonyl)-5-(benzyloxy)-8-methyl-3H-furano[3,2-e]indole (0.49 g, 1.2 mmol) dissolved in 15 mL of tetrahydrofuran (THF) under nitrogen at 0° C. were added 10% Pd/C. (0.2 g) and a 25% aqueous solution of ammonium formate (2.0 mL). This suspension was stirred at 0° C. under nitrogen for 2.5 hours. The reaction was diluted with 250 mL of diethyl ether, filtered through a plug of Celite® and concentrated under vacuum to provide 359 mg of solid (92% yield). MS (FD) m/z 337 (M+). $[\alpha]_{589}$−28.6° (c=0.35 mg/dL, $CH_2Cl_2$).

General Method for Condensation of Arylcarboxylic Acid with Alkylation Subunit (+)-(1R)-1,2-Dihydro-1-(chloromethyl)-3-(t-butyloxycarbonyl)-5-hydroxy-8-methyl-3H-furano[3,2-e]indole (1 mmol) was stirred in 23 mL of freshly prepared 3N hydrochloric acid in ethyl acetate for 30 minutes. The reaction was concentrated under vacuum. A solution of the residue, arylcarboxylic acid (1 mmol) and 1-(3-dimethylaminopropyl)-3-ethylcarbodiimide hydrochloride (3 mmol) in 20 mL of anhydrous DMF was stirred at room temperature overnight. The reaction was concentrated under vacuum, suspended in water and the precipitate collected by filtration. The residue was purified by flash chromatography with 20–40% THF/toluene.

Compound 4: (+)-(1R)-1,2-dihydro-1-(chloromethyl)-3-(2-carbonyl-5-(amino-N-(2-carbonyl-1H-indole))-1H-indole)-5-hydroxy-8-methyl-3-H furano[3,2-e]indole Anal. Calcd for $C_{30}H_{23}ClN_4O_4$: C, 66.85; H, 4.30; N, 10.39.

Found: C, 66.16; H, 4.43; N, 10.09. MS(FAB) m/z 539 (M+).
$[\alpha]_{589}$ +85.8° (c=0.5 mg/dL, DMF).

$^1$H NMR ($CD_3SOCD_3$) δ10.13 (s, 2 H), 8.18 (s, 1 H), 7.79 (s, 1 H), 7.71 (s, 1 H), 7.63 (d, J=8 Hz, 1 H), 7.53 (d, J=8 Hz, 1 H), 7.45 (s, 1 H), 7.42 (s, 1 H), 7.38 (s, 1 H), 7.17 (dd, J=8, 8 Hz, 1 H), 7.13 (s, 1 H), 7.02 (dd, J=8, 8 Hz, 1 H), 4.67 (dd, J=9, 9 Hz, 1 H), 4.52 (d, J=9 Hz, 1 H), 4.03 (m, 1 H), 3.85 (dd, J=2, 9 Hz, 1 H), 3.64 (dd, J=2, 9 Hz, 1 H), 2.32 (s, 3H).

Compound 5: (+)-(1R)-1,2-dihydro-1-(chloromethyl)-3-(2-carbonyl-5-(amino-N-(2-carbonyl[B]benzofuran))-1H-indole)-5-hydroxy-8-methyl-3H-furano[3,2-e]indole $^1$H NMR ($CD_3SOCD_3$) δ10.42 (s, 1 H), 10.12 (s, 1 H), 8.18 (s, 1 H), 7.80 (s, 1 H), 7.76 (d, J=6 Hz, 1 H), 7.70 (m, 3 H), 7.56 (d, J=7 Hz, 1 H), 7.44 (m, 2 H), 7.34 (d, J=7 Hz, 1 H), 7.14 (s, 1 H), 4.70 (t, J=6 Hz, 1 H), 4.54 (d, J=6 Hz, 1 H), 4.04 (t, J=6 Hz, 1 H), 3.90 (d, J=6 Hz, 1 H), 3.66 (t, J=6 Hz, 1 H), 2.32 (s, 1H). Anal. Calcd for $C_{30}H_{22}ClN_3O_5$: C, 66.73; H, 4.11; N, 7.78. Found: C, 66.90; H, 4.23; N, 7.58. HRMS, m/z 540.1326 ($C_{30}H_{23}ClN_3O_5$ requires 540.1326). $[\alpha]_{589}$ +76.9° (c=0.51 mg/dL, DMF).

Compound 6: (+)-(1R)-1,2-dihydro-1-(chloromethyl)-3-(2-carbonyl-5-(amino-N-(2-carbonyl[B]benzothiophene))-1H-indole)-5-hydroxy-8-methyl-3H-furano[3,2-e]indole $^1$H NMR ($CD_3SOCD_3$) δ10.24 (s, 1 H), 10.10 (s, 1 H), 8.32 (s, 1 H), 8.14 (s, 1 H), 8.02 (d, J=7 Hz, 1 H), 7.98 (d, J=7 Hz, 1 H), 7.80 (s, 1 H), 7.72 (s, 1 H), 7.56−7.40 (m, 5 H), 7.14 (s, 1 H), 4.66 (t, J=6 Hz, 1 H), 4.52 (d, J=6 Hz, 1 H), 4.02 (t, J=6 Hz, 1 H), 3.90 (s, J=6 Hz, 1 H), 3.64 (t, J=6 Hz, 1 H), 2.30 (s, 3 H). Anal. Calcd for $C_{30}H_{22}ClN_3O_4S$: C, 64.80; H, 3.99; N, 7.56. Found: C, 64.37; H, 4.09; N, 6.62. HRMS, m/z 556.1096 ($C_{30}H_{23}ClN_3O_4S$ requires 556.1098). $[\alpha]_{589}$ +73.7° (c=0.5 mg/dL, DMF).

Compound 7: (+)-(1R)-1,2-dihydro-1-(chloromethyl)-3-(2-carbonyl-5-(amino-N-(2-carbonyl-1H-indole))[B]benzofuran)-5-hydroxy-8-methyl-3H-furano[3,2-e]indole $^1$H NMR ($CD_3SOCD_3$) δ10.32 (s, 1 H), 10.16 (s, 1 H), 8.30 (s, 1 H), 7.81-7.64 (m, 7 H), 7.46−7.42 (m, 2 H), 7.19 (dd, J=8, 8 Hz, 1 H), 7.04 (dd, J=8, 8 Hz, 1 H), 4.63 (t, J =8 Hz, 1 H), 4.52 (d, J=11 Hz, 1 H), 4.03 (t, J=8 Hz, 1 H), 3.88 (d, J=11 Hz, 1 H), 3.67 (t, J=8 Hz, 1 H), 2.27 Anal. Calcd for $C_{30}H_{22}ClN_3O_5 \cdot H_2O$: C, 64.57; H, 4.33; N, 7.53. Found: C, 64.78; H, 4.35; N, 7.09. HRMS, m/z 540.1322 ($C_{30}H_{23}ClN_3O_5$ requires 540.1326). $[\alpha]_{589}$ +68.6° (c=0.35 mg/dL, DMF).

Compound 8: (+)-(1R)-1,2-dihydro-1-(chloromethyl)-3-(2-carbonyl-5-(amino-N-(2-carbonyl[B]benzofuran))[B]benzofuran)-5-hydroxy-8-methyl-3-H furano[3,2-e]indole $^1$H NMR ($CD_3SOCD_3$) δ10.16 (s, 1 H), 8.30 (s, 1 H), 7.81−7.69 (m, 9 H), 7.47 (dd, J=8, 8 Hz, 1 H), 7.34 (dd, J=8, 8 Hz, 1 H), 4.62 (t, J=9 Hz, 1 H), 4.52 (d, J=10 Hz, 1 H), 4.03 (t, J=9 Hz, 1 H), 3.87 (d, J=10 Hz, 1 H), 3.67 (t, J=9 Hz, 1 H), 2.26 (s, 3 H). Anal. Calcd for $C_{30}H_{21}ClN_2O_6$: C, 66.61; H, 3.91; N, 5.18. Found: C, 65.44; H, 4.68; N, 4.16. HRMS, m/z 541.1166 ($C_{30}H_{22}ClN_2O_6$ requires 41.1180). $[\alpha]_{589}$ +57.1° (c=0.35 mg/dL, DMF).

Compound 9: (+) (1R)-1,2-dihydro-1-(chloromethyl)-3-(2-carbonyl-5-(amino-N-(2-carbonyl[B]benzothiophene))[B]-benzofuran)-5-hydroxy-8-methyl 3H-furano[3,2-e]indole $^1$H NMR (CD$_3$SOCD$_3$) δ10.16 (s, 1 H), 8.35 (s, 1 H), 8.26 (s, 1 H), 8.04−7.97 (m, 3 H), 7.78−7.70 (m, 4 H), 7.49−7.43 (m, 3 H), 4.62 (t, J=9 Hz, 1 H), 4.52 (d, J=10 Hz, 1 H), 4.03 (t, J=9 Hz, 1 H), 3.86 (d, J=10 Hz, 1 H), 3.66 (t, J=9 Hz, 1 H), 2.26 (s, 3 H). Anal. Calcd for C$_{30}$H$_{21}$ClN$_2$O$_5$S: C, 64.69; H, 3.80; N, 5.03. Found: C, 64.84; H, 4.01; N, 4.83. HRMS, m/z 557.0919 (C$_{30}$H$_{22}$ClN$_2$O$_5$S requires 557.0938). [α]$_{589}$ +57.1° (c=0.35 mg/dL, DMF).

Compound 10: (+)-(1R)-1,2-dihydro-1-(chloromethyl)-3-(2-carbonyl-5-(amino-N-(2-carbonyl-1H-indole))[B]benzothiophene)-5-hydroxy-8-methyl-3H-furano[3,2-e]indole $^1$H NMR (CD$_3$SOCD$_3$) δ10.35 (s, 1 H), 10.14 (s, 1 H), 8.54 (s, 1 H), 8.08 (s, 1 H), 8.00 (d, J=8 Hz, 1 H), 7.78 (d, J=9 Hz, 1 H), 7.71 (s, 1 H), 7.65 (d, J=8 Hz, 1 H), 7.45 (d, J=9 Hz, 1 H), 7.43 (s, 1 H), 7.18 (dd, J=8, 8 Hz, 1 H), 7.04 (dd, J=8, 8 Hz, 1 H), 4.64 (t, J=9 Hz, 1 H), 4.41 (d, J=9 Hz, 1 H), 4.03 (m, 1 H), 3.92 (d, J=8 Hz, 1 H), 3.68 (t, J=9 Hz, 1 H), 2.26 (s, 3 H). HRMS, m/z 556.1110 (C$_{30}$H$_{23}$ClN$_3$O$_4$S requires 556.1098). α$_{589}$+117.1° (c=0.35 mg/dL, DMF).

Compound 11: (+)-(1R)-1,2-dihydro-1-(chloromethyl)-3-(2-carbonyl-5-(amino-N-(2-carbonyl[B]benzofuran))[B]benzothiophene)-5-hydroxy 8-methyl-3H-furano[3,2-e]indole $^1$NMR (CD$_3$SOCD$_3$) δ10.14 (s, 1 H), 8.57 (s, 1 H), 8.09 (s, 1 H), 8.01 (d, J=9 Hz, 1 H), 7.83−7.80 (m, 3 H), 7.78−7.72 (m, 2 H), 7.48 (dd, J=8, 8 Hz, 1 H), 7.34 (dd, J=8, 8 Hz, 1 H), 7.20−7.12 (m, 2 H), 4.67 (t, J=8 Hz, 1 H), 4.41 (d, J=9 Hz, 1 H), 4.02 (t, J=8 Hz, 1 H), 3.89 (d, J=9 Hz, 1 H), 3.68 (t, J=8 Hz, 1 H), 2.26 (s, 3 H).

Anal. Calcd for C$_{30}$H$_{21}$ClN$_2$O$_5$S: C, 64.69; H, 3.80; N, 5.03.

Found: C, 65.07; H, 4.04; N, 4.69. HRMS, m/z 557.0945

(C$_{30}$H$_{22}$ClN$_2$O$_5$S requires 557.0938). [α]$_{589}$ +108.6° (c=0.35 mg/dL, DMF).

Compound 12: (+)-(1R)-1,2-dihydro-1-(chloromethyl)-3-(2-carbonyl-5-(amino-N-(2-carbonyl[B]benzothiophene))[B]benzothiophene)-5-hydroxy-8-methyl-3H-furano[3,2-e]indole $^1$H NMR (CD$_3$SOCD$_3$) δ10.14 (s, 1 H), 8.51 (s, 1 H), 8.37 (s, 1 H), 8.08 (s, 1 H), 8.04−7.98 (m, 3 H), 7.76−7.68 (m, 3 H), 7.50−7.41 (m, 3 H), 4.66 (t, J=8 Hz, 1 H), 4.40 (d, J =9 Hz, 1 H), 3.99 (t, J=8 Hz, 1 H), 3.87 (d, J=9 Hz, 1 H), 3.67 (t, J=8 Hz, 1 H), 2.26 (s, 3 H). Anal. Calcd for C$_{30}$H$_{21}$ClN$_2$O$_4$S$_2$: C, 62.88; H, 3.69; N, 4.87. Found: C, 63.76; H, 3.92; N, 4.68. HRMS, m/z 573.0710 (C$_{30}$H$_{22}$ClN$_2$O$_4$S$_2$ requires 573.0673). [α]$_{589}$ +113.5° (c=0.52 mg/dL, DMF).

In Vitro Cytotoxicity

The cytotoxicities of 4-12 were determined by incubation (48 hours) of drug with a human squamous cell lung carcinoma (T222) and percent inhibition determined by measurement of [$^3$H]leucine uptake. T222 (Masui, et al. Cancer, 44(3): 1002-1007, 1984) human squamous carcinoma and P3/UCLA (Varki, et al., Cancer Res. 44: 681-687, 1984) human lung carcinoma cells were grown in DMEM medium supplemented with 10% fetal bovine serum and 50 ug/mL gentamicin using standard tissue culture techniques. 1×10$^4$ target cells were distributed in each well of 96 well tissue culture plates and incubated in leucine deficient medium (leucine free DMEM plus 13 ug/mL L-leucine, 29.2 ug/mL L glutamine, 50 ug/mL gentamicin and 10% dialyzed fetal calf serum) for 16 hours at 37° C. in 5% CO$_2$. The medium was then removed aseptically and compound dilutions were added in 200 ul of leucine deficient medium. Following an additional 48 hour incubation, 4 uCi $^3$H-leucine (NEN, Boston, Mass.) were added to each well and the plates were returned to the incubator for 24 hours. Radioactivity incorporated into macromolecules was determined using an automated cell harvester and liquid scintillation techniques. Data were evaluated as percent reduction in incorporation of radioactivity relative to controls incubated in medium without compound to yield an 50% cytotoxic concentration (IC$_{50}$). The IC$_{50}$'s of 4-12 in this assay were 0.17, 0.15, 0.20, 0.23, 0.37, 0.56, 0.29, 0.26 and 0.20 ng/mL; 4-desacetyl-vinblastine- 3-carboxhydrazide had an IC$_{50}$ of 3.0 ng/mL in this assay. In a similar protocol with human lung adenocarcinoma (P3/UCLA), 4 had an IC$_{50}$ of 0.27 ng/mL.

Nude Mouse Xenograft

Prior to each xenograft experiment, cells were collected by treatment with Trypsin/EDTA (Gibco, Life Technologies, Grand Island, N.Y.) and washed with supplemented DMEM and finally suspended in Hanks balanced salt solution. 1×10$^7$ cells were injected s.c. into the flank of young adult female nude mice (Charles River Breeding Laboratories, Boston, Mass.). The mice were treated by i.v. injection in the tail vein at various time points. Tumor measurements were taken in two dimensions and converted to an estimate of mass using the formula [(length) (width$^2$)/2] as described by Geran, et al.. Cancer Chemother. Rep., 3:1-103, 1972. Control groups contained 10 mice with test groups containing 5 mice each. The Student test was used to evaluate differences between mean tumor masses. When dosed at 50-200 mg/kg intravenously on days 3, 5 and 7 in the tail vein, 4 inhibited the growth of tumors in mice bearing a T222 burden (injected subcutaneously at day 0) as summarized in Table I.

TABLE I

| Efficacy of 4 in mice bearing a T222 tumor burden | | |
|---|---|---|
| Dose (mg/kg) | Percent Inhibition of Tumor Growth | Number of Deaths/ Number of Mice |
| 0.4 | | 5/5 |
| 0.2 | 85% | 1/5 |
| 0.1 | 73% | 0/5 |
| 0.05 | 68% | 0/5 |

Flow cytometric analysis of 4-6 in the T222 cell line demonstrated specificity for the G$_2$/M phase of the cell cycle at low concentration (0.1-0.5 ng/mL), but arrested the cells in the G$_0$/G$_1$ phase of the cell cycle at high concentration (5.0-10.0 ng/mL). The enantiomer of 4 was synthesized and is approximately ten fold less potent antineoplastic agent than 4 in the T222 cell line.

The compounds of Formula I are antineoplastic agents and the invention provides a method of treating susceptible neoplasms. In particular the present compounds are useful in treating solid tumors including carcinomas such as ovarian, non-small cell lung, gastric, pancreatic, prostate, renal cell, breast, colorectal, small cell lung, melanoma and head and neck; and sarcomas such as Kaposi's sarcoma and rhabdomyosarcoma.

The instant compounds can be administered individually or in combination, preferably orally, and usually in the form of a pharmaceutical composition. The instant compounds can also be used in combination with other chemotherapeutic agents. The pharmaceutical compositions of the instant compounds are prepared in a manner well known in the pharmaceutical art and comprise at least one active compound. Accordingly, the present invention also includes pharmaceutical compositions comprising as active ingredient certain compounds of Formula I associated with a pharmaceutically acceptable carrier, and the invention further comprises the method of treating susceptible neoplasms using the compositions containing as an active ingredient a compound of Formula I.

In making the compositions of the present invention, as well as compositions containing other compounds of Formula I, the active ingredients are usually mixed with an excipient, diluted by an excipient or enclosed within such a carrier which can be in the form of a capsule, sachet, paper or other container. When the excipient serves as a diluent, it can be a solid, semi-solid or liquid material which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

In preparing a formulation it may be necessary to mill the active compound to provide the appropriate particle size prior to combining with the other ingredients. If the active compound is substantially insoluble, it ordinarily is milled to a particle size of less than about 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, polyvinylpyrrolidone, cellulose, water, syrup, and methyl cellulose. The formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

The compositions of the invention can be formulated so as to provide quick, sustained or delayed release of the active ingredient after administration to the patient by employing procedures well known in the art. The compositions are preferably formulated in a unit dosage form, each dosage normally containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are effective over a wide dosage range. For example, dosages per day normally fall within the range of about 0.5 to about 1200 mg/kg of body weight. In the treatment of adult humans, the range of about 1 to about 50 mg/kg, in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following formulation examples can employ as active compounds any of the compound of Formula I. The examples are illustrative only and are not intended to limit the scope of the invention in any way.

Formulation 1

Hard gelatin capsules are prepared using the following ingredients:

|  | Quantity (mg/capsule) |
| --- | --- |
| Compound 4 | 250 |
| Starch | 305 |
| Magnesium stearate | 5 |

The above ingredients are mixed and filled into hard gelatin capsules in 560 mg quantities.

Formulation 2

A tablet formula is prepared using the ingredients below:

|  | Quantity (mg/tablet |
| --- | --- |
| Compound 5 | 250 |
| Cellulose, microcrystalline | 400 |
| Colloidal Silicon dioxide | 10 |
| Stearic acid | 5 |

The components are blended and compressed to form tablets each weighing 665 mg.

Formulation 3

A dry powder inhaler formulation is prepared containing the following components:

|  | Weight % |
| --- | --- |
| Compound 4 | 5 |
| Lactose | 95 |

The active compound is mixed with the lactose and the mixture added to a dry powder inhaling appliance.

Formulation 4

Tablets each containing 60 mg of active ingredient are made up as follows:

| Compound 6 | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 20 mesh U.S. sieve and mixed thoroughly. The solution of polyvinylpyrrolidone is mixed with the resultant powders which are then passed through a No. 4 mesh U.S. sieve. The granules so produced are dried at 50°-60° C. and passed through a No.

16 mesh U.S. sieve. The sodium carboxymethyl starch, magnesium stearate and talc, previously passed through a No. 30 mesh U.S. sieve, are then added to the granules which, after mixing, are compressed on a tablet machine to yield tablets each weighing 150 mg.

Formulation 5

Capsules each containing 80 mg of medicament are made as follows:

| Compound 7 | 80 mg |
|---|---|
| Starch | 109 mg |
| Magnesium stearate | 1 mg |
| Total | 190 mg |

The active ingredient, cellulose, starch and magnesium stearate are blended, passed through a No. 20 mesh U.S. sieve, and filled into hard gelatin capsules in 190 mg quantities.

Formulation 6

Suppositories each containing 225 mg of active ingredient are made as follows:

| Compound 8 | 225 mg |
|---|---|
| Saturated fatty acid glycerides to | 2,000 mg |

The active ingredient is passed through a No. 60 mesh U.S. sieve and suspended in the saturated fatty acid.

Formulation 7

Suspensions each containing 50 mg of medicament per 5 mL dose are made as follows:

| Compound 9 | 50 mg |
|---|---|
| Xanthan Gum | 4 mg |
| Sodium carboxymethyl cellulose (11%) Microcrystalline Cellulose (89%) | 50 mg |
| Sucrose | 1.75 g |
| Sodium Benzoate | |
| Flavor | q.v. |
| Color | q.v. |
| Purified water to | 5 mL |

The medicament, sucrose and xanthan gum are blended, passed through a No. 10 mesh U.S. sieve, and then mixed with a previously made solution of the microcrystalline cellulose and sodium carboxymethylcellulose in water. The sodium benzoate, flavor and color are diluted with some of the water and added with stirring. Sufficient water is then added to produce the required volume.

Formulation 8

Capsules each containing 150 mg of medicament are made as follows:

| Compound 10 | 150 mg |
|---|---|
| Starch | 407 mg |
| Magnesium stearate | 3 mg |
| Total | 560 mg |

The active ingredient, cellulose, starch and magnesium stearate are blended, passed through a No. 20 mesh U.S. sieve, and filled into hard gelatin capsules in 560 mg quantities.

I claim:
1. Compounds of the formula

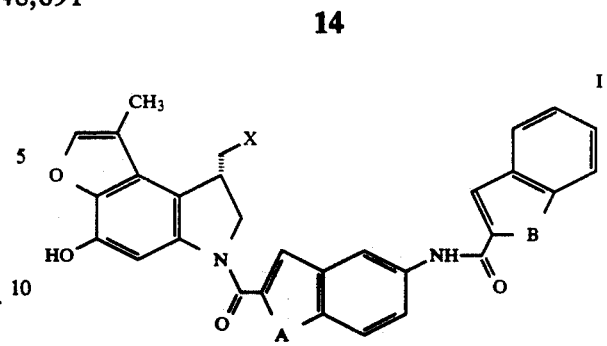

wherein
X is I, Br, Cl or OSO$_2$CH$_3$; and
A and B are independently NH, O, or S.
2. Compounds of claim 1 wherein X is chloro.
3. Compounds of claim 2 wherein A is NH.
4. The compound of claim 3 which is (+)-(1R)-1,2-dihydro 1-(chloromethyl)-3-(2-carbonyl-5-(amino-N-(2-carbonyl-1H-indole))-1H-indole)-5-hydroxy-8-methyl-3H-furano[3,2-e]indole.
5. The compound of claim 3 which is (+)-(1R) 1,2-dihydro-1-(chloromethyl)-3-(2-carbonyl-5-(amino-N-(2-carbonyl[B]benzofuran))-1H-indole)-5-hydroxy-8-methyl-3H-furano[3,2-e]indole.
6. The compound of claim 3 which is (+)-(1R)-1,2-dihydro-1-(chloromethyl)-3-(2-carbonyl-5-(amino-N-(2-carbonyl[B]benzothiophene))-1H-indole)-5-hydroxy-8-methyl-3H-furano[3,2-e]indole.
7. A method for treating susceptible neoplasms in a mammal which comprises treating a mammal in need of such treatment with an effective amount of a compound of claim 1.
8. The method of claim 7 employing a compound wherein X is chloro.
9. The method of claim 8 employing a compound wherein A is NH.
10. The method of claim 9 employing (+)-(1R)-1,2-dihydro-1-(chloromethyl)-3-(2-carbonyl-5-(amino-N-(2-carbonyl-1H-indole))-1H-indole)-5-hydroxy-8-methyl-3H-furano[3,2-e]indole.
11. The method of claim 9 employing (+)-(1R)-1,2-dihydro-1-(chloromethyl)-3-(2-carbonyl-5-(amino-N-(2-carbonyl[B]benzofuran))-1H-indole)-5-hydroxy-8-methyl-3-H-furano[3,2-e]indole.
12. The method of claim 9 employing (+)-(1R)-1,2-dihydro-1-(chloromethyl)-3-(2-carbonyl-5-(amino-N-(2-carbonyl[B]benzothiophene))-1H-indole)-5-hydroxy-8-methyl-3H-furano[3,2 e]indole.
13. A pharmaceutical formulation useful for treating susceptible neoplasms comprising an effective amount of a compound of claim 1 in combination with one or more pharmaceutically acceptable excipients, carriers, or diluents therefor.
14. A formulation of claim 13 employing a compound wherein X is chloro.
15. A formulation of claim 14 employing a compound wherein A is NH.
16. A formulation of claim 15 employing (+)-(1R)-1,2-dihydro-1-(chloromethyl)-3-(2-carbonyl-5-(amino-N-(2-carbonyl-1H-indole))-1H-indole)-5-hydroxy-8-methyl-3-H-furano[3,2-e]indole.
17. A formulation of claim 15 employing (+)-(1R)-1,2-dihydro-1-(chloromethyl)-3-(2-carbonyl-5-(amino-N-(2-carbonyl[B]benzofuran))-1H-indole)-5-hydroxy-8-methyl-3H-furano[3,2-e]indole.
18. A formulation of claim 15 employing (+)-(1R)-1,2-dihydro-1-(chloromethyl)-3-(2-carbonyl-5-(amino-N-(2-carbonyl[B]benzothiophene))-1H-indole)-5-hydroxy-8-methyl-3H-furano[3,2-e]indole.

* * * * *

UNITED STATES PATENT AND TRADEMARK OFFICE
CERTIFICATE OF CORRECTION

PATENT NO.  :  5,248,691

DATED  :  September 28, 1993

INVENTOR(S)  :  Fariborz Mohammadi

It is certified that an error appears in the above-identified patent and that said Letters Patent is hereby corrected as shown below:

Column 3, line 26, delete "carbon car", and insert therefor --carbon-car--.

Column 3, line 45, delete "1 yl", and insert therefor --1-yl--.

Column 6, line 43, delete "-8-methyl-8-methyl-", and insert therefor ---8-methyl---.

Column 7, line 11, delete "(c=0.35      mg/dL, $CH_2Cl_2$).", and insert therefor --(c=0.35 mg/dL, $CH_2Cl_2$).--.

Column 8, line 54, delete "-3-H fura-", and insert therefor ---3H-fura---.

Column 8, line 63, delete "41.1180).", and insert therefor --541.1180)--.

Column 8, line 67, delete "-methyl 3H-", and insert therefor --methyl-3H---.

UNITED STATES PATENT AND TRADEMARK OFFICE
CERTIFICATE OF CORRECTION

PATENT NO. : 5,248,691

DATED : September 28, 1993

INVENTOR(S) : Fariborz Mohammadi

It is certified that an error appears in the above-identified patent and that said Letters Patent is hereby corrected as shown below:

Column 9, line 22, delete "$\alpha_{589}$", and insert therefor --$[\alpha]_{589}$--.

Column 9, line 25, delete "hydroxy  8-methyl", and insert therefor --hydroxy-8-methyl--.

Column 9, line 27, delete "$^1$NMR", and insert therefor --$^1$H NMR--.

Column 12, line 29, delete "Quantity (mg/tablet", and insert therefor --Quality (mg/tablet--.

Column 14, line 22, delete "(1R) 1,2-", and insert therefor --(1R)-1,2---.

Column 14, line 44, delete "methyl-3-H-furano", and insert therefor --methyl-3H-furano--.

Column 14, line 59, delete " methyl-3-H-furano", and insert therefor --methyl-3H-furano--.

Signed and Sealed this

Twenty-seventh Day of December, 1994

Attest:

BRUCE LEHMAN

Attesting Officer

Commissioner of Patents and Trademarks